United States Patent
Liu

(10) Patent No.: US 10,045,916 B1
(45) Date of Patent: Aug. 14, 2018

(54) TRADITIONAL CHINESE MEDICINE MASK

(71) Applicant: Yumei Liu, New York, NY (US)

(72) Inventor: Yumei Liu, New York, NY (US)

( * ) Notice: Subject to any disclaimer, the term of this patent is extended or adjusted under 35 U.S.C. 154(b) by 0 days.

(21) Appl. No.: 15/678,111

(22) Filed: Aug. 16, 2017

(51) Int. Cl.
| | |
|---|---|
| *A61K 8/02* | (2006.01) |
| *A61K 8/67* | (2006.01) |
| *A61Q 19/00* | (2006.01) |
| *A61Q 19/08* | (2006.01) |
| *A61Q 19/02* | (2006.01) |
| *A61Q 17/00* | (2006.01) |
| *A61K 8/9728* | (2017.01) |
| *A61K 8/73* | (2006.01) |
| *A61K 8/63* | (2006.01) |
| *A61K 8/49* | (2006.01) |
| *A61K 8/98* | (2006.01) |
| *A61K 8/9789* | (2017.01) |
| *A61K 8/9722* | (2017.01) |

(52) U.S. Cl.
CPC .......... *A61K 8/0212* (2013.01); *A61K 8/4913* (2013.01); *A61K 8/4926* (2013.01); *A61K 8/63* (2013.01); *A61K 8/673* (2013.01); *A61K 8/676* (2013.01); *A61K 8/732* (2013.01); *A61K 8/9722* (2017.08); *A61K 8/9728* (2017.08); *A61K 8/9789* (2017.08); *A61K 8/987* (2013.01); *A61Q 17/005* (2013.01); *A61Q 19/00* (2013.01); *A61Q 19/007* (2013.01); *A61Q 19/02* (2013.01); *A61Q 19/08* (2013.01)

(58) Field of Classification Search
None
See application file for complete search history.

(56) References Cited

FOREIGN PATENT DOCUMENTS

CN         101669897 A    *    3/2010

* cited by examiner

*Primary Examiner* — Susan T Tran
*Assistant Examiner* — William Craigo
(74) *Attorney, Agent, or Firm* — Wayne & Ken, LLC; Tom Hom

(57) ABSTRACT

The present invention discloses a traditional Chinese medicine mask, comprising water, a Chinese traditional medicinal powder and a *Spirulina* powder. The traditional Chinese traditional medicinal powder comprises a Radix Angelicae Sinensis powder, a Flos Lonicerae powder, a Pearl powder, a Radix Angelicae Dahuricae powder, a *Bletilla Striata* powder, a Fructus Tribuli powder, a *Bombyx* Batryticatus powder, a Rhizoma Typhonii powder, a Cortex Dictamni powder and a Radix Salviae Miltiorrhizae powder. The weight percent of the traditional Chinese traditional medicinal powder is 10% to 30%, and the weight percent of the *Spirulina* powder is 2% to 5%. The present invention has following beneficial effects: anti-inflammation and anti-bacteria, prevention and healing effect, and avoiding the formation of acne scar, and has advantages of widely available natural ingredients, easy production and low cost.

10 Claims, No Drawings

TRADITIONAL CHINESE MEDICINE MASK

TECHNICAL FIELD

The present invention relates to the field of skin care products, and more specifically, to a traditional Chinese medicine mask.

BACKGROUND OF THE INVENTION

At present, most of the commonly used cosmetics are chemical synthesis products, and chemical synthesis products are generally contain different levels of lead, mercury, arsenic and other harmful substances, and the toxic and side effects of these substances often cause an allergic reaction to the user, even sequelae, so that the function of such mask is limited. Some cosmetic masks have the function of the combination of nutrients and repair, but its effect on the facial skin problem of beauty-decreasing is not obvious enough, these facial skin problems include endogenous factors such as acne, allergies, and skin damage caused by exogenous factors such as scratches, scraper, hair treatment, etc. Improper treatment of facial skin problem will easily lead to bacterial infection and inflammation and other problems in the early stage, and is easy to leave acne marks and scars in later stage. Therefore, it is necessary to improve the above deficiencies.

SUMMARY OF THE INVENTION

In order to overcome the above-mentioned deficiencies of the prior art, the present invention provides a traditional Chinese medicine mask which is safe and effective in preventing facial skin bacterial infection and repairing facial skin problem. The present invention is achieved by the following technical scheme: a traditional Chinese medicine mask comprising water, a Chinese traditional medicinal powder and a *Spirulina* powder; the Chinese traditional medicinal powder comprises a Radix Angelicae *Sinensis* powder, a Flos Lonicerae powder, a Pearl powder, a Radix Angelicae Dahuricae powder, a *Bletilla Striata* powder, a Fructus TribuliTribulus *Terrestris* powder, a *Bombyx* Batryticatus powder, a Rhizoma Typhonii powder, a Cortex Dictamni powder and a Radix Salviae Miltiorrhizae powder; a weight percent of the Chinese traditional medicinal powder is 10% to 30%, and a weight percent of the *Spirulina* powder is 2% to 5%.

Preferably, a weight percent of the Chinese traditional medicinal powder is 10% to 20%.

Preferably, a weight percent of the Pearl powder is 2% to 5%.

Preferably, the weight percent of the Chinese traditional medicinal powder is 12%, the weight percent of the Pearl powder is 2%, and the weight percent of the *Spirulina* powder is 2%.

Preferably, the weight percent of the Chinese traditional medicinal powder is 26%, the weight percent of the Pearl powder is 4%, and the weight percent of the *Spirulina* powder is 5%.

Preferably, the weight percent of the Chinese traditional medicinal powder is 17%, the weight percent of the Pearl powder is 3%, and the weight percent of the *Spirulina* powder is 3%.

Preferably, a mass ratio of the Flos Lonicerae powder, the pearl powder and the *Spirulina* powder is 2:1:1.

Preferably, the mask further comprises a mask excipient, and the mask excipient is selected from a group consisting of flour, starch or soybean meal.

Preferably, the mask further comprises a chlorpheniramine powder, a dexamethasone powder, powdered vitamin C, powdered vitamin B6, a metronidazole powder and a powdered yeast.

Preferably, the mask excipient is flour, and a weight percent of the flour is 7%.

The beneficial effects of the invention are as follows: the natural components cooperate with each other, the invention has functions of anti-inflammation and anti-bacteria, prevention and healing effect, and avoiding the formation of acne scar, whitening naturally, activating cell, improving microcirculation, enhancing metabolism, removing wrinkle and spot, soothing and moisturizing skin, lifting and firming, controlling oil, removing acne and redness, shrinking pores and delaying senility. Besides, it has advantages of widely available natural ingredients, easy production, low cost and obvious effect.

DETAILED DESCRIPTION OF THE INVENTION

The present invention will be described in more detail in the following examples, but the invention is not limited in any way.

The powder components of the embodiment of the invention are made by drying a raw material, and polishing or grounding the dired raw material into powder, so that it can be used for preparing a powder formulation.

Example 1

The present embodiment provides a traditional Chinese medicine mask, comprising Chinese traditional medicinal powder and *Spirulina* powder, the traditional Chinese traditional medicinal powder includes Radix Angelicae *Sinensis* powder, Flos Lonicerae powder, Pearl powder, Radix Angelicae Dahuricae powder, *Bletilla Striata* powder, Fructus TribuliTribulus *Terrestris* powder, *Bombyx* Batryticatus powder, Rhizoma Typhonii powder, Cortex Dictamni powder and Radix Salviae Miltiorrhizae powder, the weight percent of the traditional Chinese traditional medicinal powder is 12%, the weight percent of pearl powder is 2%, and the weight percent of the *Spirulina* powder is 2%. For convenience of use, preferably, a mask excipient is further included. And the mask excipient is selected from a group consisting of one or more of flour, starch or soybean meal, and it is mixed into a paste with water, when used, it can be directly coated on the face. Among them, the weight percent of the Flos Lonicerae powder is 2%, and the weight percentages of the Radix Angelicae *Sinensis* powder, Radix Angelicae Dahuricae powder, *Bletilla Striata* powder, Fructus TribuliTribulus *Terrestris* powder, *Bombyx* Batryticatus powder, Rhizoma Typhonii powder, Cortex Dictamni powder and Radix Salviae Miltiorrhizae powder are all 1%.

Example 2

The present embodiment provides a traditional Chinese medicine mask, comprising Chinese traditional medicinal powder and *Spirulina* powder, the traditional Chinese traditional medicinal powder includes Radix Angelicae *Sinensis* powder, Flos Lonicerae powder, Pearl powder, Radix Angelicae Dahuricae powder, *Bletilla Striata* powder, Fructus TribuliTribulus *Terrestris* powder, *Bombyx* Batryticatus powder, Rhizoma Typhonii powder, Cortex Dictamni powder and Radix Salviae Miltiorrhizae powder, the weight percent of the traditional Chinese traditional medicinal powder is 26%, the weight percent of pearl powder is 4%, and the weight percent of the *Spirulina* powder is 5%. For the convenience of use, the mask excipient is flour, the flour weight percent is 7%, and it is mixed into a paste with water, when used, it can be indirectly coated on the film carrier and then covered on the face. Among them, the weight percent of the Flos Lonicerae powder is 6%, and the weight percentages of the Radix Angelicae *Sinensis* powder, Radix Angelicae Dahuricae powder, *Bletilla Striata* powder, Fructus TribuliTribulus *Terrestris* powder, *Bombyx* Batryticatus powder, Rhizoma Typhonii powder, Cortex Dictamni powder and Radix Salviae Miltiorrhizae powder are all 2%.

In the above-described embodiment, Radix Angelicae *Sinensis* powder: it is used for promoting blood circulation and removing spot, promoting blood circulation, accelerating the discharge of exhaust gas and absorbing nutrients, anti-aging, anti-oxidation and anti-inflammation.

Flos Lonicerae powder: it has function of heat clearing and detoxifying, anti-inflammation, anti-microbial, free radical elimination and anti-oxidation, anti-aging, microcirculation improvement, peroxidized adipopexis elimination, metabolism promotion, skin moisturizing and spot removing.

Pearl powder: it is rich in varieties of amino acids and trace elements, when used in the wound, it can fill the gap tissue, vascular tissue adhesion, promote the growth of collagen in human cells, regenerate skin, anti-inflammatory, and can be used for inhibiting inflammatory cell regeneration, and preventing the wound from further deterioration.

Radix Angelicae Dahuricae powder: it has the functions of antipyretic swelling, anti-inflammatory, bacteria inibition, skin whitening, wrinkle free, pores shrinkage and so on.

*Bletilla Striata* powder: relieving redness, hemostasia, regenterating tissue, anti inflammation, anti-allergic, clearing heat, and whitening skin.

*Tribulus Terrestris* powder: it is used for improving eyesight, removing heat, relieving rash, itching, swelling and paining of the eyes, epiphora induced by wind and inhibiting the growth of bacteria.

*Bombyx* Batryticatus powder: it has the functions of relieving itching, relieving pain, removing heat, diminishing inflammation, calming and dispersing the knob, treating scar and knob, rubella, itching and softening the skin.

Rhizoma Typhonii powder: it has the effects of dispelling cold, alleviating pain, removing dampness, relieving heat, stopping pain and inhibiting toxicity, reducing light toxic reaction, anti-aging, anti inflammation, detumescence, sedation, anti inflammation, shrinking pores and whitening effect.

Cortex Dictamni powder: it has the effect of removing heat, swelling, shrinking pores, swelling of facial skin, whitening, getting rid of black and yellow, removing wrinkles, calming and removing sensitivity.

Radix Salviae Miltiorrhizae powder: it has functions of activating blood circulation to remove stasis, removing freckle, whitening and removing pigment, which is applicable to stasis of blood. And has functions of strong sedative effect, anti-inflammatory, bactericidal, anti-aging, removing wrinkles, enhancing immunity, swelling and removing redness, besides, it has a significant therapeutic effect in acne, sores, redness and swelling, peeling, cyst knot, scar skin, and so on.

*Spirulina* powder: it is rich in protein, amino acids, vitamins, unsaturated fatty acids and minerals, and has effects of improving metabolism, anti-aging skin, improving immunity, preventing skin lesions and inflammation, good adhesion and permeability, and is conducive to absorption.

The above disclosure is the preferred embodiment of the invention, it should be appreciated that any improvements and polishing without departing from the principle of the invention made by those common skilled in the art are also regarded as the scope of the invention.

Example 3

The present embodiment provides a traditional Chinese medicine mask, comprising Chinese traditional medicinal powder and *Spirulina* powder, the traditional Chinese traditional medicinal powder includes Radix Angelicae *Sinensis* powder, Flos Lonicerae powder, Pearl powder, Radix Angelicae Dahuricae powder, *Bletilla Striata* powder, Fructus TribuliTribulus *Terrestris* powder, *Bombyx* Batryticatus powder, Rhizoma Typhonii powder, Cortex Dictamni powder and Radix Salviae Miltiorrhizae powder, the weight percent of the traditional Chinese traditional medicinal powder is 17%, the weight percent of pearl powder is 3%, and the weight percent of the *Spirulina* powder is 3%. For the convenience of use, the mask excipient is soybean meal, and it is mixed into a paste with water, when used, it can be directly coated on the face. Among them, the weight percent of the Flos Lonicerae powder is 6%, and the weight percentages of the Radix Angelicae *Sinensis* powder, Radix Angelicae Dahuricae powder, *Bletilla Striata* powder, *Tribulus Terrestris* powder, *Bombyx* Batryticatus powder, Rhizoma Typhonii powder, Cortex Dictamni powder and Radix Salviae Miltiorrhizae powder are all 1%.

The present invention adopts anti-inflammatory and anti-bacterial effects of Radix Angelicae *Sinensis* powder, Flos Lonicerae powder, Pearl powder, Radix Angelicae Dahuricae powder, *Bletilla Striata* powder, Fructus TribuliTribulus *Terrestris* powder, *Bombyx* Batryticatus powder, Rhizoma Typhonii powder, Cortex Dictamni powder and Radix Salviae Miltiorrhizae powder, but also through the pearl powder and *Spirulina* powder to provide the rich nutrients and a fully nutrient extracellular environment, the present invention also provides a nutrient-rich extracellular environment by the abundant nutrients provided by the pearl powder and the *Spirulina* powder to promote the growth and regeneration of the cells, and under the action of the metabolism of Flos Lonicerae powder, it can be conducive to the healing of facial skin injury and thus not leaving acne marks and scars.

The present invention may also add appropriate amounts of targeted ingredients based on the above-described examples, such as a chlorpheniramine powder, a dexamethasone powder, powdered vitamin C, powdered vitamin B6, a metronidazole powder and a powdered yeast, these ingredients are used for solving skin acne, large pores, acne marks, excessive skin oil, red swelling and other issues. Among them, chlorpheniramine has sedative, desensitization, pores shrinkage and permeation effect; dexamethasone has the effects of reducing heat and fever, peeling and swelling resistance; vitamin B6 has a role in supplementing the skin vitamin B family, controlling oil acne, breathing permeation, and smoothing skin; metronidazole has the function of anti-inflammatory and sterilization and detumescence; yeast has the function of stopping oil, penetrating pores and diminishing inflammation; vitamin C has the role of removing heat, decomposing pigment and supplying acid.

It should be understood that one of ordinary skill in the art may be improved or modified in accordance with the foregoing description and that all such improvements and modifications are intended to be within the scope of the appended claims.

While the patent of the present invention has been described in an illustrative manner, it is obvious that the realization of the patent of the present invention is not limited by the above-described manner, and as long as the present invention has been made with various modifications or modifications of the inventive concept, the patent concept and technical scheme are directly applied to other applications within the scope of the present invention.

What is claimed is:

1. A traditional Chinese medicine mask composition, comprising
    water,
    a Chinese traditional medicinal powder, and
    a *Spirulina* powder;
    the Chinese traditional medicinal powder comprises a Radix Angelicae *Sinensis* powder, a Flos Lonicerae powder, a Pearl powder, a Radix Angelicae Dahuricae powder, a *Bletilla Striata* powder, a Fructus Tribuli, *Tribulus Terrestris* powder, a *Bombyx* Batryticatus powder, a Rhizoma Typhonii powder, a Cortex Dictamni powder and a Radix Salviae Miltiorrhizae powder;
    a weight percent of the Chinese traditional medicinal powder is 10% to 30% by weight of the composition, and
    a weight percent of the *Spirulina* powder is 2% to 5% by weight of the composition.

2. The traditional Chinese medicine mask composition of claim 1, characterized in that a weight percent of the Chinese traditional medicinal powder is 10% to 20% by weight of the composition.

3. The traditional Chinese medicine mask composition of claim 1, characterized in that a weight percent of the Pearl powder is 2% to 5% by weight of the composition.

4. The traditional Chinese medicine mask composition of claim 1, characterized in that the weight percent of the Chinese traditional medicinal powder is 12% by weight of the composition, the weight percent of the Pearl powder is 2% by weight of the composition, and the weight percent of the *Spirulina* powder is 2% by weight of the composition.

5. The traditional Chinese medicine mask composition of claim 1, characterized in that the weight percent of the Chinese traditional medicinal powder is 26% by weight of the composition, the weight percent of the Pearl powder is 4% by weight of the composition, and the weight percent of the *Spirulina* powder is 5% by weight of the composition.

6. The traditional Chinese medicine mask composition of claim 1, characterized in that the weight percent of the Chinese traditional medicinal powder is 17% by weight of the composition, the weight percent of the Pearl powder is 3% by weight of the composition, and the weight percent of the *Spirulina* powder is 3% by weight of the composition.

7. The traditional Chinese medicine mask composition of claim 1, characterized in that a mass ratio of the Flos Lonicerae powder, the pearl powder and the *Spirulina* powder is 2:1:1.

8. The traditional Chinese medicine mask composition of claim 1, characterized in that the mask further comprises a mask excipient, and the mask excipient is selected from a group consisting of flour, starch or soybean meal.

9. The traditional Chinese medicine mask composition of claim 1, characterized in that the mask further comprises a chlorpheniramine powder, a dexamethasone powder, powdered vitamin C, powdered vitamin B6, a metronidazole powder and a powdered yeast.

10. The traditional Chinese medicine mask composition of claim 8, characterized in that the mask excipient is flour, and a weight percent of the flour is 7% by weight of the composition.

* * * * *